US00PP18403P2

(12) United States Plant Patent
Meadows, Jr. et al.

(10) Patent No.: US PP18,403 P2
(45) Date of Patent: Jan. 8, 2008

(54) ***RAPHIOLEPIS INDICA* PLANT NAMED 'SODARK'**

(50) Latin Name: *Raphiolepis indica*
Varietal Denomination: Sodark

(75) Inventors: Thomas Dennis Meadows, Jr., Silverhill, AL (US); James Bryan Berry, Grand Saline, AL (US)

(73) Assignee: Plant Development Services, Inc., Loxley, AL (US)

( * ) Notice: Subject to any disclaimer, the term of this patent is extended or adjusted under 35 U.S.C. 154(b) by 0 days.

(21) Appl. No.: 11/488,650

(22) Filed: Jul. 19, 2006

(Under 37 CFR 1.47)

(51) Int. Cl.
*A01H 5/00* (2006.01)

(52) U.S. Cl. ..... Plt./254

(58) Field of Classification Search ..... Plt./254
See application file for complete search history.

*Primary Examiner*—Kent Bell
*Assistant Examiner*—Annette H Para
(74) *Attorney, Agent, or Firm*—Breiner & Breiner, LLC

(57) ABSTRACT

A new and distinct variety of *Raphiolepis indica* named 'Sodark' found as an openly pollinated seedling of *Raphiolepis indica* 'Conor' U.S. Plant Pat. No. 9,398. The new variety is unique with its dense, mounding growth habit, attractive leaf shape, dark foliage color, and abundance of dark pink flowers.

1 Drawing Sheet

Genus species: *Raphiolepis indica.*
Varietal denomination: 'Sordark'.

BACKGROUND OF THE INVENTION

The present invention relates to a new and distinct variety of the genus *Raphiolepis* and a member of the Rosaceae family. This new *Raphiolepis* variety, hereinafter referred to as 'Sodark' was discovered by Thomas Dennis Meadows, Jr. and James Bryan Berry in June, 2000. 'Sodark' was found as an openly pollinated seedling of *Raphiolepis indica* 'Conor' U.S. Plant Pat. No. 9,398, maintained by Plant Development Services Inc. in Loxley, Ala. The value of this new cultivar lies in its dense, mounding growth habit, attractive leaf shape, dark foliage color, and abundance of dark pink flowers. The new variety has retained many of the outstanding attributes of its parent cultivar, in particular its tolerance of heat, drought, salt, and disease, which makes it adaptable to culture in most of the Sunbelt States. As with the parent cultivar, the plant of this invention may be advantageously employed as a specimen appointment, a ground cover, in either formal or informal groupings, and is quite attractive in mass plantings. 'Sodark' serves well in foundation plantings and is adaptable for culture as a potted plant. 'Sodark' is responsive to pruning and training and may be employed in forming dense, attractive hedges, and maintained without an excessive amount of care. This plant is easy to care for and maintain in size due to its short internodes, heavy branching, and dense canopy. Its natural propensity to remain small to maturity makes it valuable for landscape uses in smaller home gardens which require plants that do not outgrow their intended mature dimensions.

Asexual propagation of the new plant by cuttings has been under Mr. Meadows' direction in Loxley, Ala. The new plant retains its distinctive characteristics and reproduces true to type in successive generations of asexual reproduction. The plant cannot be reproduced true from seed.

SUMMARY OF THE INVENTION

The following are the most outstanding and distinguishing characteristics of this new cultivar when grown under normal horticultural practices in Loxley, Ala.

1. Dense and mounding in nature. Plant is wider than tall.
2. Mature leaves are a lustrous dark green color in the spring and summer with purple undertones in the fall and winter.
3. Mature leaves are coriaceous, undulate, slightly upturned, and have a distinct revolute margin.
4. The flowers are single, dark pink, fragrant, and profuse.
5. Moderate to slow growth rate, requiring little pruning.
6. Hardy to Zone 7b.
7. Heat and drought tolerant.
8. Adaptable to a wide range of soil types.
9. Good plant for coastal areas because of wind and salt tolerance.
10. Has shown good resistance to leaf spot and fireblight.
11. Relatively pest resistant.
12. Good specimen plant.
13. Good foundation plant.
14. Makes a very good low-growing hedge.
15. Very desirable in planters.
16. Produces seeds and therefore may result in bird visitations.

DESCRIPTION OF THE DRAWINGS

This new *Raphiolepis indica* variety is illustrated by the accompanying photographic prints in which:

FIG. 1 is a photograph of a close-up showing the flower, buds, foliage and stem color, as well as flower size and form.

FIG. 2 is a photograph showing the dense and mounding growth habit of a three gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Raphiolepis* based on observations made of two year old plants grown in three gallon containers in wholesale commercial production practices, in greenhouses, and in established landscape plantings in Loxley, Ala. and including a comparison with *Raphiolepis indica* 'Conor' U.S. Plant Pat. No. 9,398, and *Raphiolepis indica* 'Hines Darkleaf' U.S. Plant Pat. No. 8,635.

Distinctive Characteristics:

TABLE 1

| Characteristic | *Raphiolepis i.* 'Sodark' | *Raphiolepis i.* 'Conor' PP#9398 | *Raphiolepis i.* 'Hines Darkleaf' PP#8635 |
|---|---|---|---|
| Height (Mature) | 2-3 feet | 3-4 feet | 2-2½ feet |
| Width (Mature) | 3-4 feet | 4-5 feet | 6+ feet |
| Leaf Length | 2⅛-1⅞ inches | 2-3 inches | 3 inches |
| Leaf Width | ⅞-1¼ inches | 1-1¼ inches | 1¼ inches |
| Leaf Margin | Entire | Serrate-Crenate | Entire |
| Leaf Tip | Obtuse | Acute | Cuspidate |
| Leaf Base | Alternate to Cuneate | Alternate to Cuneate | Narrow Cuneate |
| Leaf Curvature | Undulate w/ Revolute Margin | Undulate w/ Revolute Margin | Recurved |
| Winter Foliage (Mature) | Closest to Yellow-Green G. 147A w/ Greyed-Purple G. 187A undertones | Yellow-Green G. 147A | Closest to Greyed-Purple G. 187A w/ Black undertones |
| Flower | Single | Semi-Double | Single |
| Flower Color | Red-Purple G. 68A | Red-Purple G. 65B | Red G. 54C |
| Petal Number | 5 | 5-8 | 5 |
| Petal Shape | Elliptical | Oblanceolate | Ovate |

*Raphiolepis indica* 'Sodark', *Raphiolepis indica* 'Conor' U.S. Plant Pat. No. 9,398, and *Raphiolepis indica* 'Hines Darkleaf' U.S. Plant Pat. No. 8,635 are cultivars of Rosaceae *Raphiolepis indica.* The author of the genus name *Raphiolepis* is John Lindley (1799–1865). The original author of the species name *Indica* is Carlolus Linnaeus (1707–1778) and the name was transferred to the plant *Raphiolepis indica* by John Lindley. The new variety 'Sodark' was found in 2000 as an openly pollinated seedling of *Raphiolepis indica* 'Conor'.

*Raphiolepis indica* 'Conor' and *Raphiolepis indica* 'Hines Darkleaf' are well known in the industry and are comparable to 'Sodark' in that all are compact growers. However, there are many differences. The foliage of 'Sodark' is slightly smaller than 'Conor' or 'Hines Darkleaf'. The mature winter foliage color of 'Sodark' is closest to but darker than Yellow-Green Group 147A and has Greyed-Purple Group 187A undertones. 'Hines Darkleaf' is near to Greyed-Purple Group 187A and has black undertones. The mature winter foliage of 'Conor' is Yellow-Green Group 147A. The flower color of 'Sodark' is a darker pink than 'Conor' or 'Hines Darkleaf.'

Classification:
Botanical: *Raphiolepis indica* 'Sodark'.
Parentage: Openly pollinated seedling of *Raphiolepis indica* 'Conor'.
Commercial: Broadleaf evergreen.
Form: Dense and mounding.
Height: 2–3 feet.
Width: 3–4 feet.
Growth rate: Moderate to slow under normal fertilization and moisture conditions. Semi-hardwood cuttings taken in late spring and through the summer produce rooted cuttings in three to four months in Loxley, Ala. Root development is vigorous and finely branched. In a period of six years from a rooted cutting, the plant reaches a height of 2 feet and a spread of 3 feet under normal growing conditions in Loxley, Ala. The plant normally grows at the rate of about 4 inches or more per year and reaches a height of 3 feet and a spread of 4 feet at maturity while maintaining a dense habit due to the abundant branch development.
Foliage: Alternate, simple, evergreen, elliptic to obovate, and varying in size from 2⅛ inches to 2⅞ inches long and ⅞ inch to 1¼ inches wide. The petioles are ¼ inch to ½ inch long and 1/16 inch in diameter. The midrib is prominent on both sides of the leaf and the veins are prominent on the underside. Veins are depressed on the upper side giving a leathery appearance. The base of the leaf is attenuate to cuneate, the margin entire, and the apex is obtuse. The upper surface of the mature leaf is closest to but darker than Yellow-Green Group 147A, glossy and glabrous. The underside is Yellow-Green Group 146B and matte. These mature leaf colors are persistent throughout the winter. Immature foliage (including petioles, midribs, and veins) which emerges in the cool spring and fall is tomentulose and noticeably pigmented Greyed-Purple Group 187A upper and lower surface. Foliage (including midribs and veins) which emerges during warmer weather is tomentulose with upper leaf surface Greyed-Orange Group 165A. This foliage changes to Green Group 137A and matures closest to Yellow-Green Group 147A in three to four weeks in Loxley, Ala. The midribs mature to Yellow-Green Group 147B upperside and Yellow-Green Group 146D underside. The veins mature to Yellow-Green Group 147B upperside and underside. The lower leaf surface is Greyed-Orange 165B and matures to Yellow-Green Group 146B. Petioles emerging during warmer months are tomentulose, Greyed-Purple Group 187D upperside, Yellow-Green Group 146C underside and mature to Yellow-Green Group 146B both sides. The paired foliaceous stipules are 3/16 inch to 5/16 inch long and 1/16 inch to ⅛ inch wide. The upper surface is Yellow-Green Group 145A and the underside is Yellow-Green Group 145B. The stipules are caducous.

The mature foliage of 'Sodark' is similar to the parent variety in that both are coriaceous with undulate and revolute margins. As with the parent variety, the leaves at the branch tips are held upward and appear whorled, similar to *Pittosporum tobira.* This undulate leaf shape, revolute margin, and whorled appearance adds greatly to the attractiveness of the new variety.

In 2003, the date of initial spring growth was March 3, in Loxley, Ala. After the initial spring flush there was almost continuous slow growth until fall, ending October 21, also in Loxley, Ala. When grown in full sun, the internode length of this plant is ¼ inch to ½ inch. When grown in light shade the internode length is ⅜ inch to ¾ inch. As would be expected, a plant grown in the shade results in a taller, less dense plant with larger leaves.

Stems: The young shoots have a deep purple pigmentation, Greyed-Purple Group 187A, and are tomentulose. This new growth becomes Yellow-Green Group 146A in three to four weeks. After one or more years, the stems are generally grey (Greyed-Green Group 197B), glabrous, and rugose. The pith is solid and uniform.

Flowers: Perfect, single, glabrous, ¾ inch in diameter by ⅜ inch in depth, fragrant, borne on dense, upright, tomentulose, 3 to 4 inches high and 2 to 3 inches wide terminal panicles from late March to April. Each panicle has from 3–6 racemes which have from 1–8 flowers each, resulting in thirty or more flowers per panicle. A mature plant can have 100 or more panicles. Flower color is Red-Purple Group 68A upper surface and Red-Purple Group 68B under surface. The lower ⅛ inch of each petal is White Group 155D upper surface and under surface. After two to three days the flower changes to Red-purple Group 65B, upper and under surface, and after five to seven days the whole flower matures to White Group 155D. The flowers are attached to short pedicels which are 3/16 inch to ⅜ inch in length and Yellow-Green Group 144B. The peduncle of each raceme is from ½ inch to 2½ inches long and Yellow-Green Group 144B. Each flower has 5 petals that are ⅜ inch long, ¼ inch wide, elliptical, and have obtuse tips. The flower has from 15 to 20 stamens, ¼ inch long, White Group 155C, with anthers Yellow Group 10B. The pollen matures to yellow Group 9C. The pistil is ¼ inch long, White Group 155C, and consists of two styles which are united and have ciliate margins. The base of the stamens and pistil change Red-Purple Group 63B two to three days after opening. Each flower has five sepals that are ⅛ inch long, 1/16 inch wide, lanceolate, and fused into a calyx. The calyx is ¼ inch in diameter, ⅜ inch in depth, Greyed-Purple Group 185A (inner surface and outer surface), has ciliate margins and acuminate tips. In 2003, the blooming period began March 14, in Loxley, Ala. and ended April 28. The self-cleaning blooms last eight to ten days on the plant in the garden.

Fruit: Drupaceous, globose, ¼ inch to ⅜ inch in diameter, 1 to 2 seeded. Summer fruit color Yellow-Green Group 144A ripens to Greyed-Purple Group 187A in the fall and persists as Black Group 202A attractively through the winter. Mature seeds are Greyed-Orange Group 163A beneath the pericarp.

Culture: Grows well in a wide range of conditions and tolerates sun to part shade. Grows in nearly any soil type, from moist to very dry and sand to clay. Responds well to mulching and medium applications of fertilizer; prefers pH 6 to 7. Very little pruning is needed. Adaptable to containers and above ground planters. Ideal for coastal regions and warmer parts of the Piedmont. Tolerates wind and salt spray. Propagated with semi-hardwood cuttings in late spring through the summer.

Pests: None have been observed to date. The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claim.

It is claimed:

1. A new and distinct variety of *Raphiolepis* plant named 'Sodark' as illustrated and described.

* * * * *

FIGURE 1
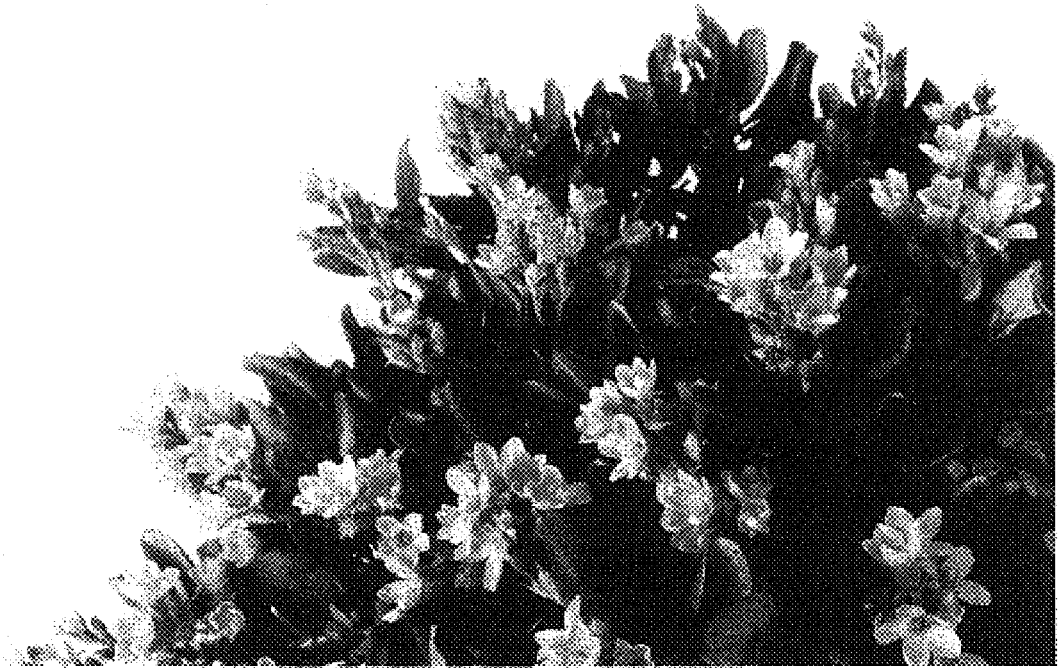
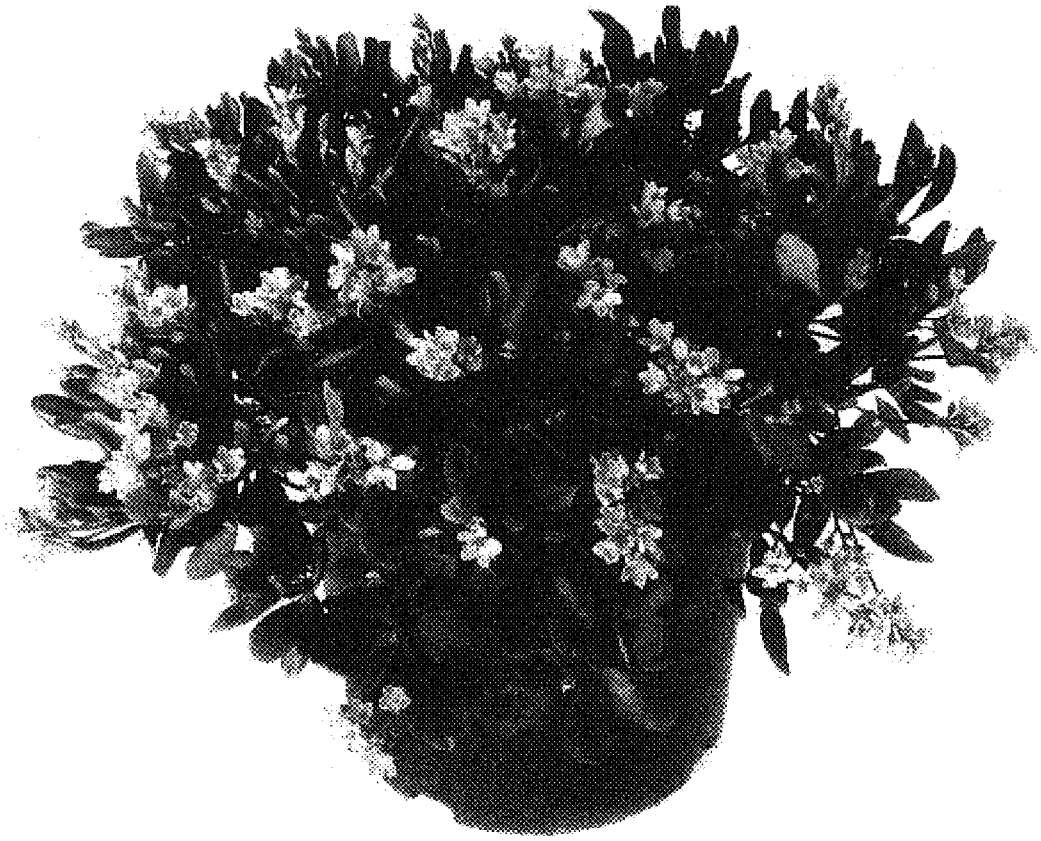
FIGURE 2